(12) United States Patent
Hegenbart et al.

(10) Patent No.: US 9,934,896 B2
(45) Date of Patent: Apr. 3, 2018

(54) INSPECTION APPARATUS AND INSPECTION SYSTEM FOR INSPECTING ACCESS-RESTRICTED SPACES AND AREAS

(71) Applicant: Airbus Operations GmbH, Hamburg (DE)

(72) Inventors: Matthias Hegenbart, Hamburg (DE); Peter Linde, Hamburg (DE); Detlev Konigorski, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 0 days.

(21) Appl. No.: 15/348,337

(22) Filed: Nov. 10, 2016

(65) Prior Publication Data
US 2017/0133135 A1    May 11, 2017

(30) Foreign Application Priority Data
Nov. 11, 2015   (EP) .................................... 15194075

(51) Int. Cl.
| H01F 6/00 | (2006.01) |
| H01F 7/02 | (2006.01) |
| H02N 15/04 | (2006.01) |
| G01N 21/88 | (2006.01) |
| G01N 27/90 | (2006.01) |

(Continued)

(52) U.S. Cl.
CPC ........... *H01F 7/0294* (2013.01); *G01N 21/88* (2013.01); *G01N 21/954* (2013.01); *G01N 27/9006* (2013.01); *H01F 6/00* (2013.01); *H01F 6/04* (2013.01); *H01F 7/06* (2013.01); *H01F 7/20* (2013.01); *H02N 15/04* (2013.01); *G01N 27/902* (2013.01)

(58) Field of Classification Search
CPC ....................... G01N 21/88–2121/9586; G01N 27/90–27/9093; H01F 6/00–6/065; H01F 7/206; H01F 2007/208; H02N 15/00–15/04
See application file for complete search history.

(56) References Cited

U.S. PATENT DOCUMENTS

| 5,631,617 A | 5/1997 | Morishita |
| 6,005,460 A | 12/1999 | Garrigus et al. |

FOREIGN PATENT DOCUMENTS

| EP | 0695027 A1 | 1/1996 |
| EP | 1709438 A1 | 10/2006 |

(Continued)

OTHER PUBLICATIONS

European Search Report, Extended European Search Report for European Patent Application No. 15194075.6 dated Apr. 15, 2016.

*Primary Examiner* — Ramon M Barrera
(74) *Attorney, Agent, or Firm* — Lorenz & Kopf, LLP

(57) ABSTRACT

This relates to an inspection apparatus for inspecting a structural component to which access is restricted, comprising a movable unit including a superconductor and an inspection device, a drive unit including a magnetic field generator adapted to generate a magnetic field, wherein said movable unit and said drive unit are arranged with a predetermined gap therebetween for receiving said structural component and are coupled in a force-locking manner by means of the frozen magnetic flux, i.e., without a physical connection, between the magnetic field generator and the superconductor. Thus, spaces or areas to which access is restricted can be inspected without the need of physically connecting the drive unit and the movable unit.

15 Claims, 6 Drawing Sheets

(51) Int. Cl.
*H01F 6/04* (2006.01)
*H01F 7/20* (2006.01)
*G01N 21/954* (2006.01)
*H01F 7/06* (2006.01)

(56) References Cited

FOREIGN PATENT DOCUMENTS

| EP | 2045600 A1 | 4/2009 |
| JP | 2006044829 A | 2/2006 |

INSPECTION APPARATUS AND INSPECTION SYSTEM FOR INSPECTING ACCESS-RESTRICTED SPACES AND AREAS

CROSS-REFERENCE TO RELATED APPLICATION

This application claims priority to European Patent Application No. 15194075.6, filed Nov. 11, 2015, which is incorporated herein by reference in its entirety.

TECHNICAL FIELD

This relates to an inspection apparatus and an inspection system using one or more such inspection apparatuses for inspecting spaces/areas and structural components to which access is restricted or is not easily available. The embodiment finds a particular application in the aerospace industry but is by no means limited thereto.

BACKGROUND

An inspection of areas or spaces to which access is restricted is necessary in many industries and technical fields. Some simple examples in FIG. 7 illustrate the problem of access restriction. FIG. 7A shows a simple wall or structural component W1 of a considerable size such that it might be difficult to easily inspect the backside thereof, for example if the wall W1 is quite high and only accessible from the top T. FIG. 7B shows another example of a wall W2 to which access is restricted because the back side of the wall is accessible only from one side A whilst the inner space (hollow space) is access-restricted on three other sides B, C and D because of solid walls. Whilst the front surface of the wall W2 maybe visually (or e.g. via infrared sensing or laser sensing) inspected to detect for example mechanical defects, it is difficult to inspect (or analyze) the back side of the wall W2 because the opening A might not be wide enough for a human being to crawl into it or the wall W2 might simply be too high such that it would at least be cumbersome to a person to climb up the wall on one side and struggle down the other side if the side B was accessible (as discussed with reference to FIG. 7A).

There may be also other reasons why access to certain areas or spaces behind the wall W1 or W2 is restricted. For example, the interior space may be polluted with hazardous gases such that a human being must not enter the restricted space for health reasons. It could also be that fire has developed inside the space or behind the wall and this does not allow immediate access. In such a case, the inspection might not simply relate to inspecting the structural component or the inside wall itself but to inspecting the interior space as to whether or not there is trapped a human being who needs assistance.

In cases of such area or space access restrictions, an inspection device, for example a camera, must be inserted into the space differently. Conventional solutions, for example in the field of pipe inspection, comprise the use of a small robot crawling into the piping or into the space to which access is restricted for human beings. Such a robot can be remote-controlled and may be equipped with a camera. For smaller spaces, it might be sufficient to fix an inspection device to the end of a holding rod and then to physically move around the inspection device by moving the holding rod.

In the aerospace industry, inspection of various structural components is essential before, and in particular, after assembly and during maintenance. For example, in the aircraft many access-restricted areas exist as hollow spaces in the wings or elsewhere in the fuselage. In addition, the inner mechanical structure of a wing is quite complicated and involves various different support structures. In such a case, typically a manhole is provided somewhere to provide access to the inner space and a human being crawls into this access-restricted space, for example into a wing or a tank after degassing. On the other hand, exactly because the wing comprises complicated support structures inside it is also not easily possible to have a robot driving around inside the wing for inspection.

SUMMARY

As explained above, in many industries it is necessary to inspect areas or spaces or structural components to which an access is restricted, i.e. not easily possible, for whatever reason such that an inspection device cannot easily be placed or moved around for inspection. Furthermore, in many cases an inspection by human beings might be cumbersome or at least time-consuming or dangerous.

Therefore, an advantage of the present embodiment is to provide an inspection apparatus and an inspection system for allowing inspection of access-restricted areas or spaces in an easy manner.

According to a first aspect, an inspection apparatus is provided for inspecting a structural component to which access is restricted, comprising a movable unit including a superconductor and an inspection device, a drive unit including a magnetic field generator adapted to generate a magnetic field, wherein said movable unit and said drive unit are arranged with a predetermined gap there-between for receiving said structural component and are coupled in a force-locking manner by means of the frozen magnetic flux between the magnetic field generator and the superconductor.

According to the first aspect, the movable unit and the drive unit are force-locked by means of the frozen flux established between the superconductor of the movable unit and the magnetic field generator of the drive unit. The frozen flux acts as a kind of artificial rod such that the drive unit can move the movable unit which carries the inspection device substantially three-dimensionally along any desired path. The rod, i.e. the force-coupling between the drive unit and the movable unit, is a contactless rod and therefore the movable unit with the inspection device can be placed easily within a space or area to which access is restricted whilst the movable unit can be guided from outside by the drive unit with the magnetic field generator and through the frozen flux coupling. Therefore, the embodiment avoids that for example a visual inspection needs to be done by humans (mechanics, engineers, pilots).

The magnetic field generator described herein may comprise a permanent magnet, an electromagnetic device, or a superconducting magnet. With any of these embodiments, if the drive unit is moved along a predetermined movement path, the movable unit is moved along the same predetermined path by means of said force-locked coupling through the frozen magnetic field.

The inspection device described herein may be a camera or an eddy-current device or any other device suitable for an inspection of the structural component or hollow space.

It is particularly advantageous if the drive unit comprises a first control device adapted to control the magnetic field generator to generate the frozen flux. In this case, the magnetic field generator may generate the magnetic field with a particular direction and strength. If the first control device controls the magnetic field strength, the gap between the superconductor and the magnetic field generator can be adjusted as desired. In this manner, the moveable unit cannot only be moved along a predetermined path in a direction substantially perpendicular to the direction of force coupling but also the distance (gap) between the drive unit and the movable unit can be adjusted. Therefore, through the adjustment of the magnetic field, a fully three-dimensional floating of the movable unit can be achieved.

Preferably, the structural component or the hollow space or area to which access is restricted is a hollow aerospace component such as a wing, an omega stringer, a tank, a rocket, a tube or an engine. If the embodiment is used for an aerospace component, it can be avoided that manholes of a certain minimum size and assembled with fasteners need to be provided. This saves additional weight which is in particular important for aerospace components. It also avoids that sealing problems in the area of manholes in the aerospace components occur. Furthermore, an inspection in hazardous areas and spaces can be performed. For example in tanks, an inspection can be performed even before outgassing.

The movable unit and/or the drive unit may comprise one or more sensor devices. In a preferred embodiment the sensor devices are arranged in the movable unit to sense the geometry of the structural component and a transmission unit of the movable unit is adapted to transmit the geometrical or positional data to the first control device, wherein the first control unit is adapted to control movement of the drive unit in accordance with the positional data transmitted from the movable unit. In this manner, a fully-automated inspection can be carried out.

The drive unit may drive the movable unit through the force-locked coupling via the frozen magnetic flux to perform a rotation or translation. The drive unit may be movable in two perpendicular directions, in a plane substantially perpendicular to the forced-coupling between the movable unit and the drive unit.

The inspection device may transmit inspection data to a monitoring device wirelessly and the sensor devices may likewise transmit positional or geometrical data wirelessly. In this manner, the inspection device or respectively the movable unit only has to be placed within the space or area to which access is restricted without the need of extending a wiring to the movable unit.

The inspection apparatus may comprise several drive units, each with a magnetic field generator. Several magnetic field generators may generate a larger magnetic field which will result in a stronger coupling between the drive unit and the movable unit.

According to a second aspect, an inspection system is provided for inspecting a space, area or structural component to which access is restricted, comprising one or more inspection apparatuses as explained above. The inspection system further comprises a movement device adapted to move the drive unit along a predetermined movement path. The movement path can be two-dimensional or three-dimensional because the frozen flux coupling will (as long as the magnetic field strength remains constant) hold the movable unit at a constant gap width even if the drive unit is moved by the movement device arbitrarily in space.

The movement device may comprise guide rails for guiding the drive unit along the predetermined movement path. Thus, the drive unit with the magnetic field generator is easily moved in X and Y directions.

Further advantageous embodiments and improvements of the embodiment are listed in the dependent claims.

BRIEF DESCRIPTION OF THE DRAWINGS

The various embodiments will hereinafter be described in conjunction with the following drawing figures, wherein like numerals denote like elements, and.

The figures are schematic and are not necessarily true to scale. If, in the following description the same reference signs are used in the context of different figures, they refer to similar or equivalent elements. Similar or equivalent elements may, however, also be referenced with different reference signs.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1:
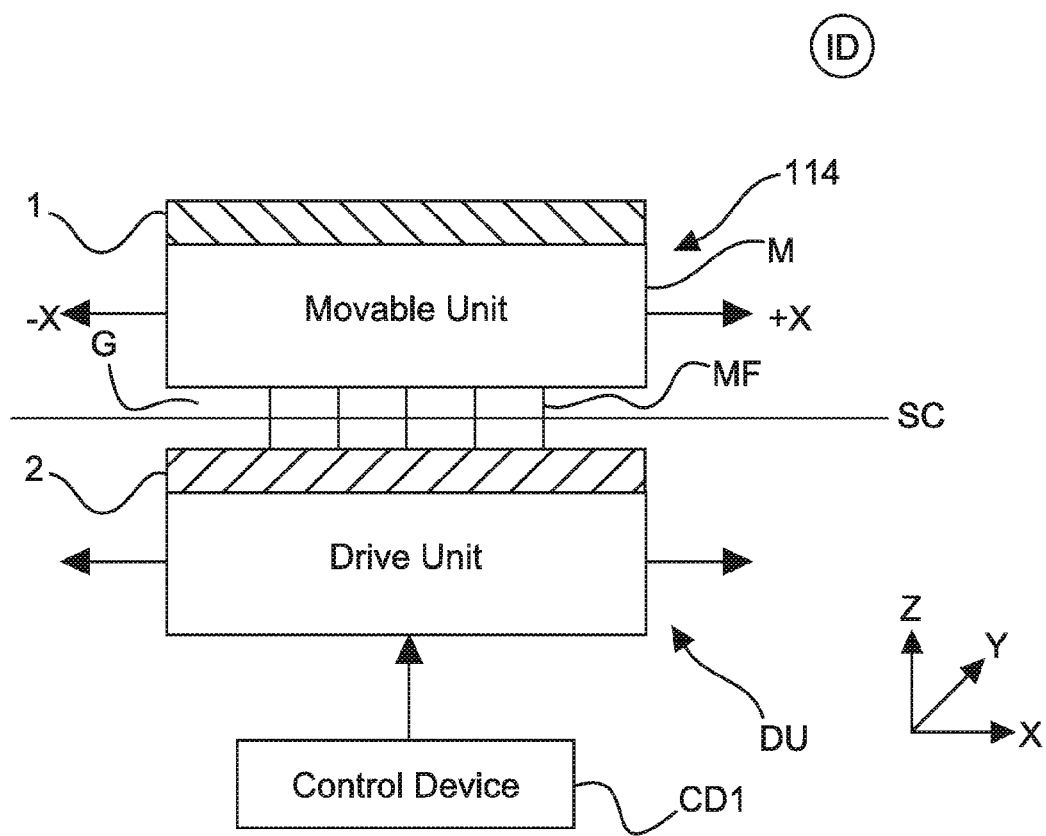
FIG. 1 illustrates an inspection apparatus ID for inspecting a structural component SC to which access is restricted, according to an exemplary embodiment.

FIG. 1 shows an inspection apparatus ID comprising a movable unit MU carrying an inspection device 1 and including a superconductor block M. The movable unit MU can be moved along a predetermined direction X which in FIG. 1 is shown to be the horizontal direction. The inspection apparatus ID further comprises a drive unit DU carrying a magnetic field generator 2. As shown in FIG. 1, the movable unit MU and the drive unit DU are arranged with a predetermined gap G therebetween for substantially receiving the structural component SC. The movable unit MU and the drive unit DU are coupled in a forced-locking manner by means of the frozen magnetic flux between the magnetic field generator 2 and the superconductor block M. A control device CD1 may be used for controlling the drive unit DU and in particular the magnetic field generator 2. The magnetic field generator 2 generates a magnetic field MF directed to the superconductor block M.

In FIG. 1, a space or area which needs to be inspected by the inspection device 1 is for example the back surface (in FIG. 1 the upper surface) of the structural component SC. However, the inspection device 1 may inspect also other components and devices or structural defects generally arranged in the space "behind" the structural component SC.

Thus, the structural component SC is only illustrative for illustrating that access to the area or space which needs inspection is restricted, i.e. not immediately accessible to the inspection device 1. There is also no restriction how the movable unit MU is placed "behind" the structural component SC or generally within the space or area to which access is restricted. Thus, it should be generally understood that the movable unit MU and the drive unit DU are arranged with a gap G therebetween for generally receiving the structural component SC which prevents or partially restricts access to the area or space behind the structural component.

The frozen magnetic field is the result of the Meissner-Ochsenfeld effect occurring in a superconductor when a magnetic field of sufficient strength is applied thereto and if the superconductor is cooled below its critical temperature. As is well known to the skilled person, below the critical temperature a superconductor does not only change its electric conductivity. Below the critical temperature a superconductor can also store or "freeze" the magnetic field generated by a permanent magnet (or generated by any other means). To illustrate the effect of the frozen magnetic flux: if a non-magnetic distance rod is placed between the magnet and the superconductor and the superconductor is cooled below its critical temperature and the rod is removed, the superconductor will float stably above the magnet. If the superconductor is shifted, it will always return to its "stored" position. In this manner, the movable unit which carries the inspection device 1 will substantially float above the drive unit DU which includes the magnetic field generator 2. The strength of the force-locked coupling of course depends on the superconducting material, the amount of cooling and the magnetic field strength of the magnetic field MF. The control device CD1 may be provided to adjust the gap width G in which the structural component SC is received. In fact, by adjusting the strength of the magnetic field, the distance between the movable unit MU and the drive unit DU can be adjusted. In this manner, the drive unit DU can not only move the movable unit MU in a plane substantially perpendicular to the force-locking direction between the drive unit DU and the movable unit MU, but it can also vary the distance therebetween.

Figure 7A:
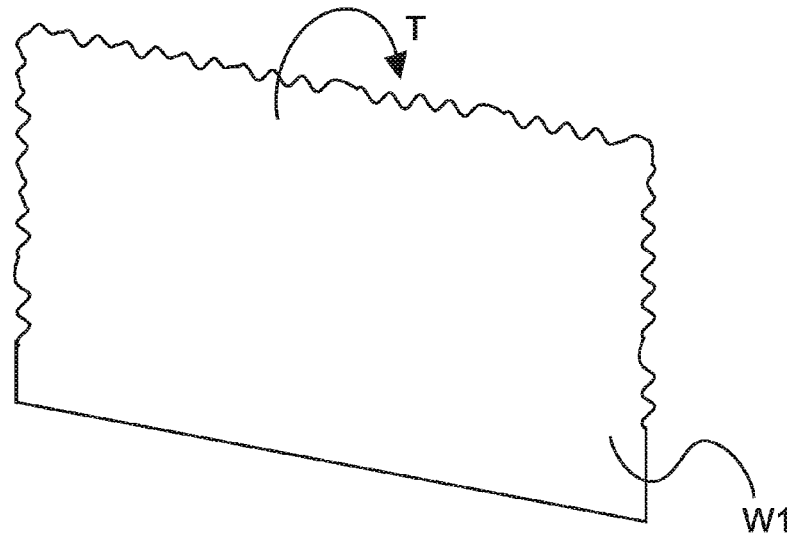
FIG. 7A and FIG. 7B illustrate the problems with conventional inspection apparatuses for inspecting a wall or a hollow space to which access is restricted.
Figure 7B:
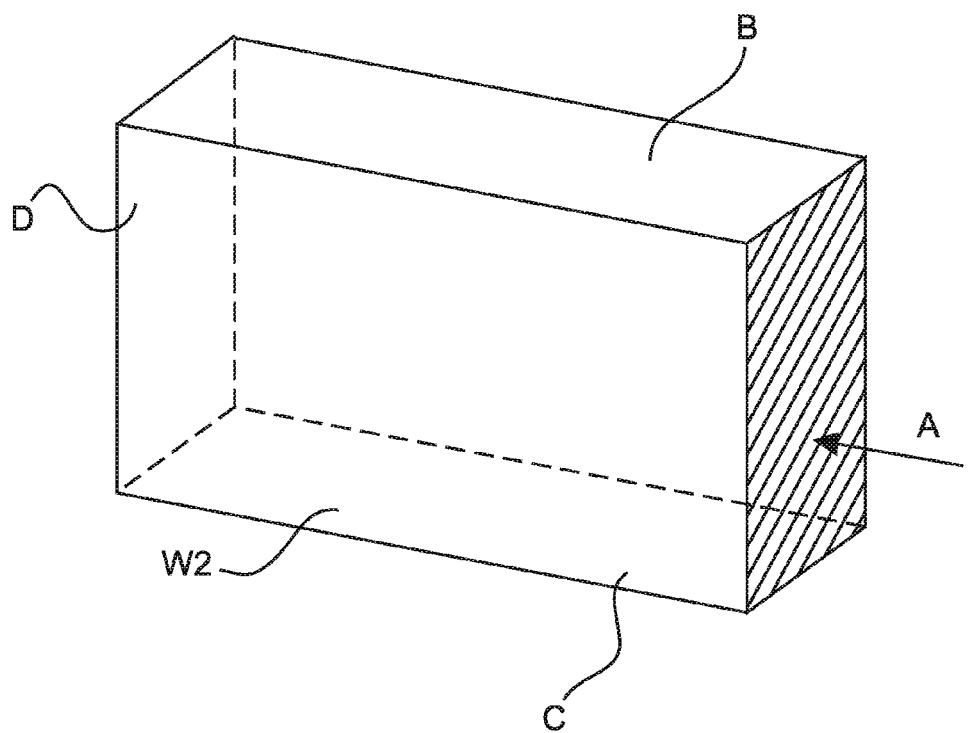

Through the frozen magnetic flux, the movable unit MU and the drive unit DU are really force-locked. If the movable unit is moved in a predetermined direction X, also the drive unit DU will be moved. Likewise, if the drive unit DU is moved, the movable unit MU is moved. The force-locking with the frozen flux exhibits a kind of elasticity like a mechanical spring. However, the force-locking or force-coupling can be made so intensive, that elasticity is almost zero, depending on the strength of the magnetic field and the type of superconductor. Therefore, depending on the weight of the movable unit MU and the inspection device 1 always a magnetic field can be generated which will keep the movable unit MU substantially floating. In this manner, the inspection device ID according to the exemplary embodiment replaces the conventional mechanical coupling (as explained with reference to FIG. 7) or the necessity of human inspection through manholes by means of a contactless magnetic field guided inspection.

It may be noted that the force-coupling or force-locking allows not only translatorial movements but also rotational movements in any plane, depending on the movement path of the drive unit DU. Thus, movement of the movable unit MU may not only take place in the X and Y directions in FIG. 1 but also in a rotational manner along the X or Y or Z directions. As already mentioned above, the magnetic field strength may be adjusted by the control device CD1 to also vary the gap width G between the drive unit DU and the movable unit MU in the Z direction.

Hence, as apparent from FIG. 1, by controlling the magnetic field it is possible to inspect internal volumes of components controlled and steered from outside the compartment. Due to the contactless guidance it is not necessary to have full access to the compartment; only a small opening is needed for insertion of the inspection device 1 because nowadays superconductors as well as their cooling devices for cooling to the critical temperature are available in small sizes down to the size of a small shoebox. The external guidance of the drive unit DU may be pre-programmed in accordance with the internal geometries to be inspected known beforehand or measured during inspection with sensors as described with more details below with reference to FIG. 3.

The movable unit MU comprises the superconducting material block M. On the other hand, the magnetic field generation by the magnetic field generator 2 can be done in any preferred manner, for example by a permanent magnet, an electromagnetic device or also by a superconducting magnet. As long as the magnetic field strength is sufficient to cause the force-coupling, whenever the drive unit is moved along a predetermined movement path, the movable unit is moved along a corresponding path by means of the force-locked coupling. Typical magnetic field strengths generated by the magnetic field generator 2 are in the order of 1 Tesla.

Figure 3:
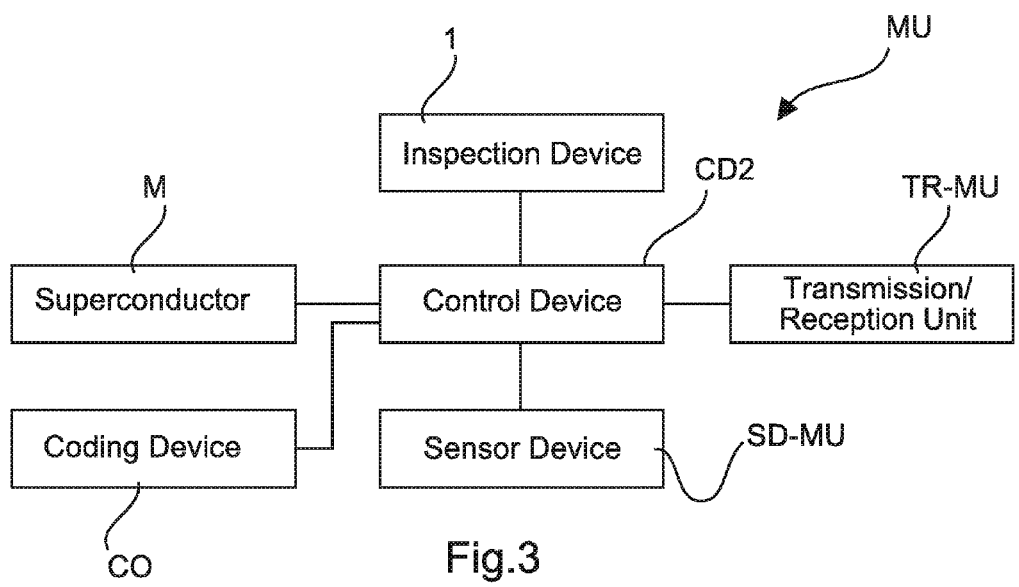
FIG. 3 illustrates a block diagram of a movable unit MU according to an exemplary embodiment.

Any inspection device 1 can be carried by the movable unit M. Hence, the inspection device 1 may be a simple camera, a laser device, a CCTV or CCD camera or an eddy-current device. The inspection device may also be a VIS, an IR sensor or any other measurement or inspection device using other physical principles for inspection, depending on the circumstances. As shown in FIG. 3, the movable unit MU may further comprise a cooling device for cooling the semiconductor M to a critical temperature at which it is superconducting. The cooling device CO for the super conducting material block M may comprise liquid nitrogen.

In FIG. 1, as an illustrative example, the structural component SC is shown to be arranged between the movable unit MU and the drive unit DU to illustrate the access restriction.

However, it is to be understood that the structural component SC or any other barrier which restricts access to the space or area or structural component to be inspected must be non-magnetic or at least not substantially non-magnetic such that the magnetic field lines MF can penetrate the structural component SC.

A typical example where the embodiment is advantageous is in the aerospace industry. Many structural components in the aerospace industry are made of non-magnetic material; for example the structural component SC may be a wing, an omega-stringer, a tank, a rocket, a tube, or an engine. In particular, the structural component SC may be a hollow aerospace component, for example the inside of a wing, of a tank etc. to which there is limited accessibility. The inspection apparatus ID of the embodiment does not require the provision of manholes of a certain minimum size and also disposes the need of fasteners for providing the manholes. Furthermore, the inspection apparatus ID may be used in hazardous environments, such as tanks for fuel of the aeroplane. Thus, tanks can already be inspected before outgassing of hazardous gases in tanks. Furthermore, indirectly of course the inspection device ID reduces the costs and the weight because there is no need for manhole fasteners. Furthermore, since no fasteners are provided, they do not have to be inspected.

Although, as explained, the inspection apparatus ID has particular application in the aerospace industry, any other space or area to which access is restricted may be inspected, as long as the barrier which prevents access is non-magnetic. Such applications may, therefore, be found similarly in the automotive industry, for the inspection of non-magnetic pipes or other technical fields.

Figure 2A:
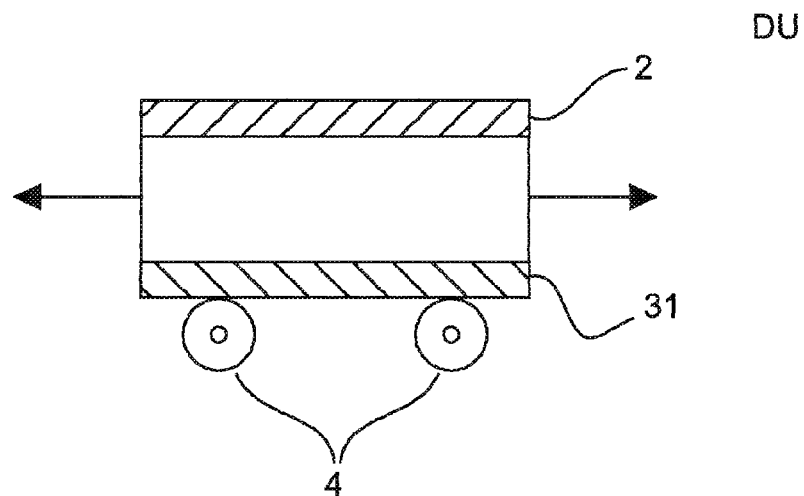
FIG. 2A illustrates an embodiment of the drive unit DU carrying the magnetic field generator 2 and being movable in a predetermined direction.
Figure 2B:
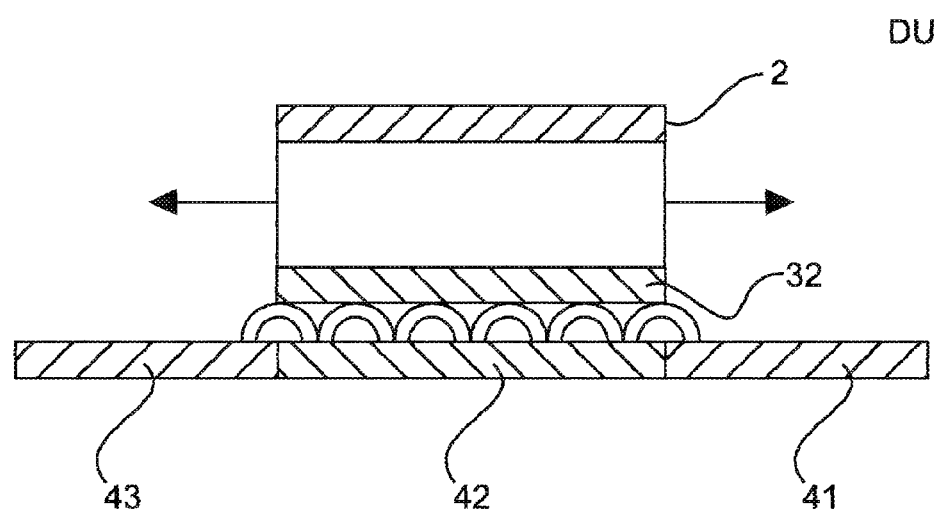
FIG. 2B illustrates another embodiment of the drive unit DU being moved by a plurality of switchable magnets 41-43.

FIG. 2A and FIG. 2B show preferred embodiments of the drive unit DU. In FIG. 2A the drive unit DU comprises a movement unit 31 including rollers 4. In this manner, if the drive unit DU is moved in X or Y direction on the rollers 4, the movable unit MU will likewise be moved in the same predetermined direction (along the same predetermined path). In FIG. 2B the movement unit 32 is a magnet which lies opposite a plurality of magnets 41, 42, 43 which can be arranged to generate a magnetic field for transporting the drive unit in a predetermined direction X. Such magnetic transport drive arrangements and principles are known from trains running on magnetic tracks or other movement mechanisms. The magnetic drive arrangement 32, 41-43 is particularly advantageous because there is no friction and the drive unit DU can easily be moved along a predetermined programmed path.

FIG. 3 shows a block diagram of the movable unit MU. It comprises a second control device CD2, an inspection device 1 as previously discussed, a transmission unit TR-MU, one or several sensor devices SD-MU, the superconducting block M and a cooling device CO already mentioned above. The control device CD2 controls the cooling device CO such that the magnetic field is frozen inside the superconducting block M. As explained above, the control device CD2 will control the cooling device CO to cool the superconductor to a temperature below its critical temperature.

The control device CD2 can also control the inspection device 1, for example to switch on and off an illumination to illuminate a dark space if a camera is used as the inspection device 1 in a dark hollow space, for controlling the camera and for taking certain measurements. A preferred embodiment of the inspection device 1 is an infrared sensor, a Hall sensor, a VIS or eddy-current measurement devices as mentioned above. Further preferred embodiments of the inspection device 1 comprise touch sensors which sense the surface of the structural component back side.

The control device CD2 also cooperates with one or more sensor devices SD-MU. The sensor devices SD-MU may be arranged in the movable unit MU to sense the geometry of the inner space of the structural component SC. The sensor devices SD-MU may also simply detect the position of the moveable unit MU in the hollow space. The sensor devices SD-MU may also comprise touch sensors, similarly as the inspection device, for generating positional data. In this manner, if for example the inner geometry of the hollow space (such as a wing) is known, the positional data can indicate the position of the movable unit MU inside the hollow space in an accurate manner with respect to certain blocking support structures, for example in an aircraft wing. The sensor devices SD-MU may also comprise sensors for detecting the humidity, temperature, certain types of gases and other environmental conditions. A particularly advantageous sensor device comprises sensors for detecting the build-up of electric fields which are for example particularly dangerous in aerospace components.

Figure 4:
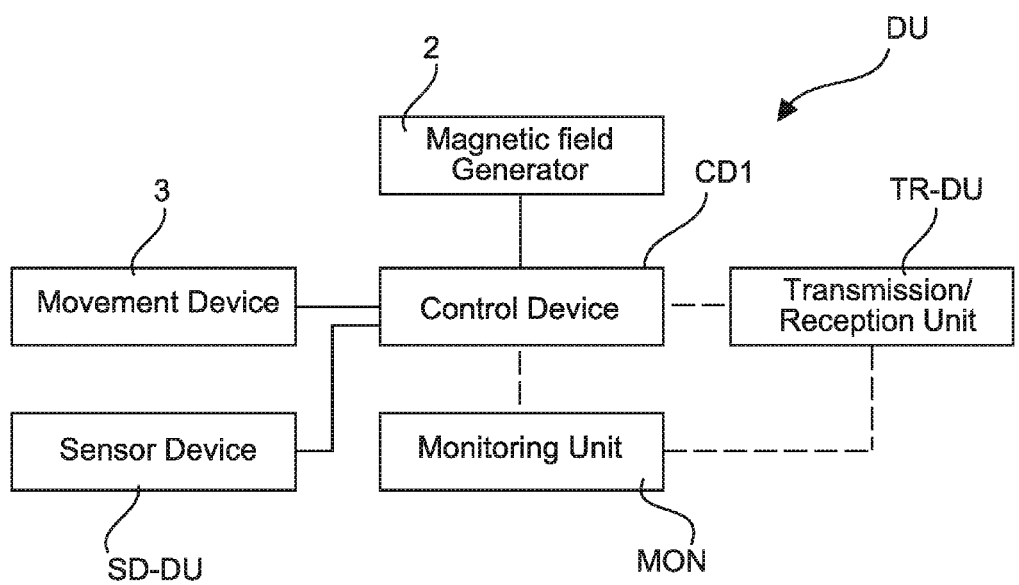
FIG. 4 illustrates a block diagram of the drive unit DU according to an exemplary embodiment.

The second control device CD2 receives the inspection data and other sensor data respectively from the inspection device 1 and the sensor devices SD-MU and supplies this data to the transmission unit TR-MU. The transmission/reception unit TR-MU is adapted to transmit the data (positional data and inspection data) to the drive unit DU. As shown in FIG. 4, an embodiment of the drive unit DU also comprises a transmission/reception section TR-DU which forwards the received data to the first control device CD1 and a monitoring device MON. When the first control unit CD1 receives the data from the movable unit MU, it may control the movement of the drive unit DU in accordance with the sensor data, for example positional data, transmitted from the transmission unit TR-MU of the movable unit MU. The transmission technique for forwarding the data between the movable unit MU and the drive unit DU may be a wireless transmission technique, for example through infrared connections or via radio. Such transmission techniques may further comprise a Bluetooth connection.

The monitoring device MON does not have to be part of the drive unit DU itself but may be placed at a separate location and may forward the data through the control device CD1. The monitoring unit MON may be a simple mobile communication device (mobile telephone) or a monitoring station comprising computer hardware and software. The monitoring device MON may comprise a display unit (not shown in FIG. 4) on which the inspection results can be displayed. For example, the monitoring unit MON may display a graphic illustration of the hollow space, for example of the inside of a wing, together with the movement path of the movable unit MU. Along the illustrated path certain data recorded by the inspection device 1 or the sensor devices SD-MU can be displayed.

Above it has already been described above that the drive unit DU, in a preferred embodiment, will be controlled by the first control device CD1 depending on positional data received from the movable unit MU. However, it is also possible that in the control device CD1 of the drive unit DU a predetermined path is pre-programmed and that the drive unit DU is controlled dependent on the pre-programmed path without considering the positional data from the sensor devices SD-MU. The receipt of the positional data from the sensor device SD-MU is particularly advantageous because a kind of feed-back loop can be established in which the movement of the drive unit DU is controlled in a closed-loop manner on the basis of the positional data received from the movable unit MU.

In the block diagram of the drive unit DU in FIG. 4, the first control device CD1 may control the movement unit 3 (see e.g. the movement units 31 and 32 in FIG. 2A and FIG. 2B either in accordance with the predetermined and pre-programmed path, or dependent on the received positional data from the movable unit MU. Additionally, the drive unit DU itself may also comprise sensor devices SD-DU. Such sensor devices SD-DU can preferably sense the start and end position of the drive unit DU. In accordance with another embodiment the sensor devices SD-DU can sense a predetermined path along which the drive unit DU is to be moved. For example, the sensor devices SD-DU may sense a predetermined geometry and drive the drive unit DU to follow this geometry and to consequently cause the movable unit MU to prescribe a path in accordance with the geometry sensed by the sensor devices SD-DU. However, also other embodiments of the sensor devices are possible.

The transmission/reception unit TR-DU may also be adapted to receive control signals from a remote controller. In accordance with the control signals received by the transmission/reception unit TR-DU, the control device CD1 may control the movement unit 3 to move the drive unit DU in a particular manner along a predetermined path determined by the control signals. As was explained with reference to FIG. 1, such movement can be translatorial or rotational along any axis and also in connection with an adjustment of the electromagnetic field strength so as to vary the gap width G. For example, the remote controller may be a joystick device arranged at the monitoring device MON to control movement of the drive unit DU in the X, Y and Z directions since, as explained before, the "floating" movement of the movable unit MU is fully three-dimensional. For example, the movement of the drive unit DU may comprise a circle around the fuselage of an aeroplane or any other movement whilst the movable unit MU is coupled (force-coupled) with the drive unit DU.

Figure 5:
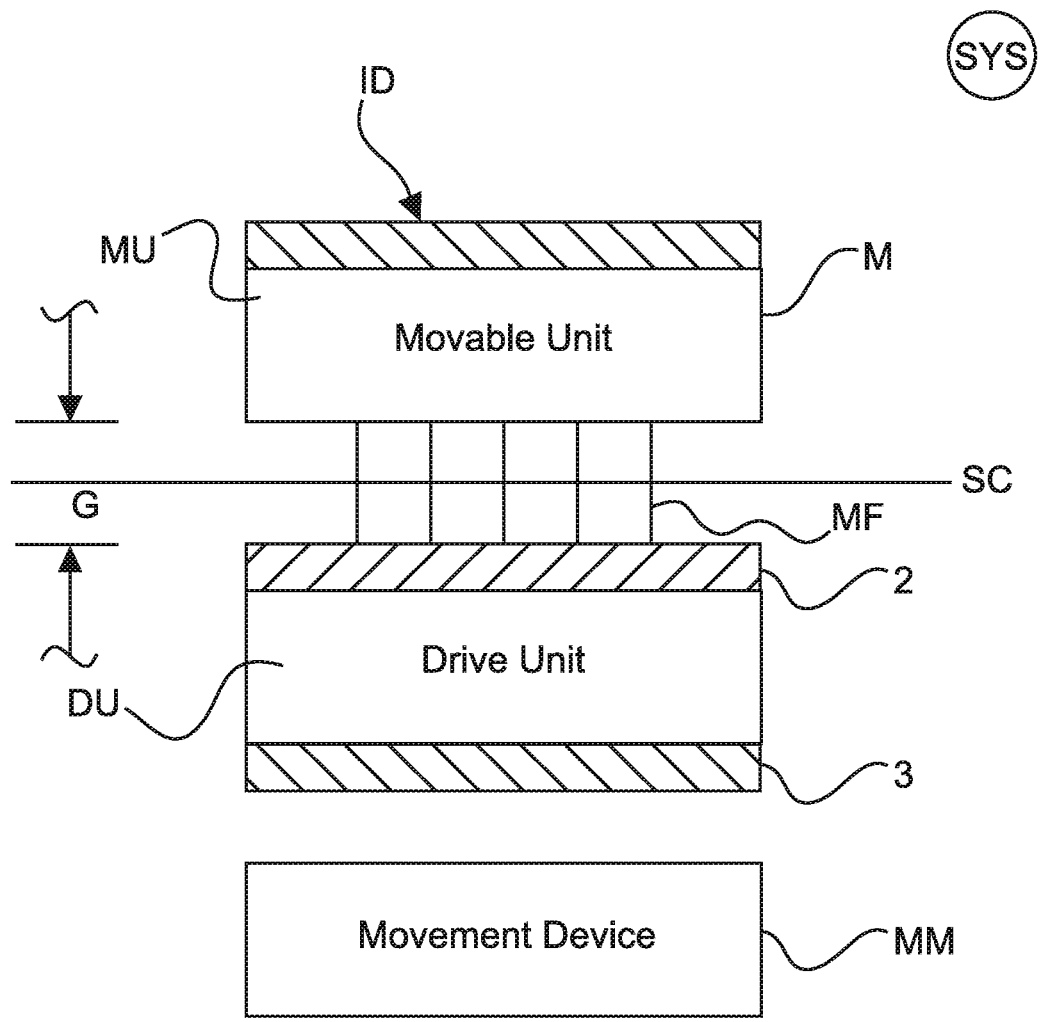
FIG. 5 illustrates an inspection system SYS including a movement device MM for moving the drive unit DU according to an exemplary embodiment.

FIG. 5 shows an embodiment of the inspection system SYS according to the embodiment for inspecting a structural component SC to which access is restricted. The inspection system SYS comprises one or more inspection apparatuses as shown in FIG. 1. Each drive unit DU comprises a movement unit 3 as was explained in principle with respect to FIG. 2 and FIG. 4. The inspection system SYS further comprises a movement device MM adapted to move the drive unit DU along the predetermined movement path. Hence, the movement unit 3 of the drive unit DU and the movement device MM cooperate in order to have the drive unit DU—and hence also the movable unit MU through the force-locking by means of the frozen flux—prescribe a predetermined inspection path.

Figure 6:
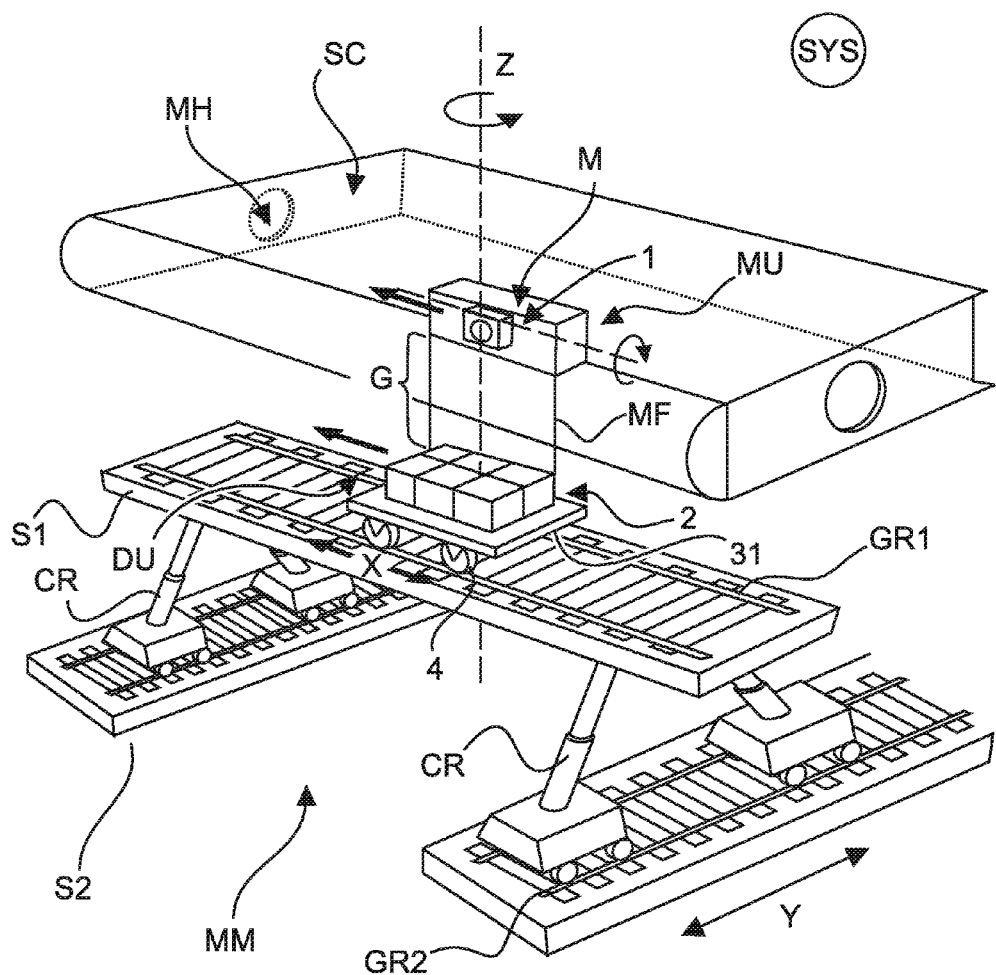
FIG. 6 illustrates an exemplary embodiment of the inspection system SYS including a movement device MM realized by guide rails GR1, GR2.

FIG. 6 shows an inspection system SYS of what the inventors currently regard as a best mode of the embodiment. In FIG. 6 the structural component SC is a hollow space, for example a part of a wing or fuselage of an aircraft having a manhole MH. Of course, as explained above, in accordance with the embodiment such a man hole MH can be made much smaller than a manhole conventionally provided in such aerospace components. For example, the structural component SC may be an aerospace structural box. The movable unit MU comprises the superconducting material block M which carries the inspection device 1. By an appropriate adjustment of the magnetic field strength generated by the magnetic field generator 2 the movable unit MU is force-locked in a predetermined gap width G with respect to the magnetic field generator 2. The magnetic field generator 2 is placed on a movement unit 31 comprising rollers 4 as explained with reference to FIG. 2A. In FIG. 6 the movement device MM comprises guide rails GR1, GR2 for guiding the drive unit DU along a predetermined movement path in the X and Y directions. In fact, the rollers 4 of the drive unit DU roll on the guide rails GR1 in the X direction and the guide rail GR1 is connected through the supports CR to a perpendicularly-arranged guide rail GR2 extending in the Y direction. In this manner, by moving the drive unit DU along the X direction on the guide rail GR1 and by moving the guide rail GR1 in the Y direction on the guide rail GR2, a fully two-dimensional movement in the X, Y plane can be performed. As explained above, by adjustment of the magnetic field strength, also the gap width G may be adjusted.

Although FIG. 6 only shows the X, Y movement of the drive unit DU, it should be understood that in principle any mechanical, electrical or other movement device MM may be used such that the drive unit DU prescribes any predetermined path. For example, the drive unit DU may be rotated along the Z axis extending through the magnetic field generator 2 and the drive unit DU. It is also feasible that the drive unit DU movement prescribes a circular movement around an axis X' extending through the superconducting material block M. In this manner, the movable unit MU may be rotated or translated in any predetermined direction which allows a full inspection of the interior of the aerospace structural (hollow) box SC.

Depending on the geometry of the structural component SC or depending on the needs for the internal inspection, the movement device MM may simply comprise a robot arm to the drive unit DU is fixed and which can be easily moved along the X, Y, Z directions according to need such that the inspection device and the movable unit MU will perform a corresponding movement.

In the claims, the word "comprising" does not exclude other elements or steps and the indefinite article "a" or "and" does not exclude a plurality. The mere fact that certain measures are recited in mutually different dependent claims does not indicate that a combination of these measures cannot be used to advantage. Reference numerals in the claims only serve clarification purposes and do not limit the scope of the claims.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

What is claimed is:

1. An inspection apparatus for inspecting a structural component to which access is restricted, comprising:
   a movable unit including a superconductor and an inspection device;
   a drive unit including a magnetic field generator adapted to generate a magnetic field; wherein
   said movable unit and said drive unit are arranged with a predetermined gap therebetween for receiving said structural component and are coupled in a force-locking manner by means of the frozen magnetic flux between the magnetic field generator and the superconductor; and
   wherein the magnetic field strength is adapted to keep the movable unit substantially floating three-dimensionally.

2. The apparatus according to claim 1, wherein the magnetic field generator comprises a permanent magnet, an electromagnetic device or a superconducting magnet.

3. The apparatus according to claim 1, wherein when said drive unit is moved along a predetermined movement path, said movable unit is moved along the same predetermined path by means of said force-locked coupling.

4. The apparatus according to claim 1, wherein said inspection device is a camera or an eddy-current device.

5. The apparatus according to claim 1, wherein said drive unit comprises a first control device adapted to control the magnetic field generator to generate the frozen flux.

6. The apparatus according to claim 3, wherein said first control device is adapted to control the gap width by means of controlling the magnetic field strength.

7. The apparatus according to claim 1, wherein said structural component is a hollow aerospace component selected from the group consisting of a wing, an omega stringer, a tank, a rocket, a tube and an engine.

8. The apparatus according to claim 1, wherein said movable unit and/or said drive unit comprise one or more sensor devices.

9. The apparatus according to claim 8, wherein the sensor devices arranged in the movable unit are adapted to sense the geometry of the structural component and a transmission unit of said movable unit is adapted to transmit corresponding positional data to the first control unit, wherein said first control unit is adapted to control movement of the drive unit in accordance with the positional data transmitted from the movable unit.

10. The apparatus according to claim 1, wherein the drive unit, through the force-locked coupling via the frozen magnetic flux, drives the movable unit to perform a translation or rotation.

11. The apparatus according to claim 1, wherein the drive unit is movable in two perpendicular directions.

12. The apparatus according to claim 1, wherein said structural component is a hollow component and the inspection device transmits inspection data to a monitoring device wirelessly.

13. The apparatus according to claim 1, wherein said apparatus comprises several drive units each with a magnetic field generator.

14. An inspection system for inspecting a structural component, comprising one or more inspection apparatuses according to claim 1, and further comprising a movement device adapted to move the drive unit along a predetermined movement path with the movable unit kept substantially floating three-dimensionally.

15. An inspection system according to claim 14, wherein said movement device comprises guide rails for guiding the drive unit along the predetermined movement path.

* * * * *